(12) United States Patent
Messner et al.

(10) Patent No.: US 6,565,981 B1
(45) Date of Patent: May 20, 2003

(54) POLYMERS THAT ARE CROSS-LINKABLE TO FORM SUPERABSORBENT POLYMERS

(75) Inventors: Bernfried Messner, Greensboro, NC (US); Whei-Neen Hsu, Greensboro, NC (US); Robert Agne, Greensboro, NC (US)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 09/280,458

(22) Filed: Mar. 30, 1999

(51) Int. Cl.[7] .............................. C08J 3/28; B32B 23/00; B32B 27/04; B32B 27/16; B05D 3/06
(52) U.S. Cl. .................... 428/441; 428/442; 428/476.3; 428/483; 428/507; 428/511; 428/516; 522/86; 525/903; 525/919; 526/930
(58) Field of Search .............................. 427/2.31, 498, 427/499, 512, 513, 521; 428/441, 442, 476.3, 483, 507, 511, 516; 522/86; 525/903, 919; 526/930

(56) References Cited

U.S. PATENT DOCUMENTS

| | | | |
|---|---|---|---|
| 3,311,583 A | 3/1967 | Bearden ..................... 260/29.6 |
| 3,719,647 A | 3/1973 | Hardy et al. ............... 260/86.1 |
| 3,884,964 A | 5/1975 | Otrhalek et al. ......... 260/486 R |
| 3,926,891 A | 12/1975 | Gross et al. ............... 260/29.6 |
| 3,980,663 A | 9/1976 | Gross ......................... 260/29.6 |
| 3,995,998 A | 12/1976 | Rowland et al. ............. 8/115.6 |
| 4,041,020 A | 8/1977 | Gross ......................... 260/79.3 |
| 4,041,121 A | 8/1977 | Smith ......................... 264/191 |
| 4,057,521 A | 11/1977 | Gross ......................... 260/29.6 |
| 4,066,584 A | 1/1978 | Allen et al. ................. 260/17.4 |
| 4,071,650 A | 1/1978 | Gross ......................... 428/260 |
| 4,076,928 A | 2/1978 | Gross ......................... 526/240 |
| 4,104,214 A | 8/1978 | Meierhoefer ............... 260/17.4 |
| 4,128,692 A | 12/1978 | Reid | |
| RE30,029 E | 6/1979 | Smith ......................... 128/285 |
| 4,218,692 A | 8/1980 | de Cremoux ................. 357/19 |
| 4,351,922 A | 9/1982 | Yoshida et al. ............. 525/116 |
| 4,354,487 A | 10/1982 | Oczkowski et al. | |
| 4,381,320 A | 4/1983 | Nguyen | |
| 4,431,769 A | 2/1984 | Yoshida et al. ............. 524/555 |
| 4,500,315 A | * 2/1985 | Pieniak et al. | |
| 4,524,186 A | 6/1985 | Nagase ..................... 525/328.8 |
| 4,703,998 A | 11/1987 | Uchioke et al. .......... 350/96.23 |
| 4,725,655 A | 2/1988 | Denzinger et al. ............ 526/65 |
| 4,764,554 A | 8/1988 | Tonge ......................... 524/559 |
| 4,800,220 A | 1/1989 | Ribba ..................... 526/238.23 |
| 4,812,491 A | 3/1989 | Hahn, Jr. ..................... 523/310 |
| 4,815,813 A | 3/1989 | Arroyo et al. ............ 350/96.23 |
| 4,861,539 A | 8/1989 | Allen et al. ................. 264/204 |
| 4,886,852 A | 12/1989 | Numa ......................... 524/458 |
| 4,909,592 A | 3/1990 | Arroyo et al. ............ 350/96.23 |
| 4,913,517 A | 4/1990 | Arroyo et al. ............ 350/96.23 |
| 4,914,170 A | * 4/1990 | Chang et al. | |
| 4,957,806 A | 9/1990 | Pangrazi et al. ............. 428/224 |
| 4,962,172 A | 10/1990 | Allen et al. .............. 526/318.42 |
| 5,100,397 A | * 3/1992 | Poccia et al. | |
| 5,133,034 A | 7/1992 | Arroyo et al. ............... 385/107 |
| 5,147,956 A | 9/1992 | Allen ..................... 526/318.42 |
| 5,229,466 A | 7/1993 | Brehm et al. ............. 525/329.9 |
| 5,280,079 A | 1/1994 | Allen et al. ............... 525/329.2 |
| 5,328,935 A | * 7/1994 | Van Phan et al. | |
| 5,342,686 A | * 8/1994 | Guersen et al. | |
| 5,389,442 A | 2/1995 | Arroyo et al. ............... 428/396 |
| 5,390,273 A | 2/1995 | Rahman et al. ............. 385/112 |
| 5,408,019 A | 4/1995 | Mertens et al. ............. 526/240 |
| 5,409,771 A | 4/1995 | Dahmen et al. ............. 428/327 |
| 5,481,635 A | 1/1996 | Arroyo et al. ............... 385/103 |
| 5,534,304 A | * 7/1996 | Geursen et al. | |
| 5,610,220 A | 3/1997 | Klimmek et al. ........... 524/417 |
| 5,635,569 A | * 6/1997 | Sackmann et al. | |
| 5,642,452 A | 6/1997 | Gravely et al. ............. 385/113 |
| 5,869,178 A | 2/1999 | Kusy et al. ................. 428/335 |

FOREIGN PATENT DOCUMENTS

| | | | |
|---|---|---|---|
| CA | 1286465 | 7/1991 | |
| CA | 1329305 | 5/1994 | |
| DE | 25 46 392 | 4/1976 | |
| EP | 0 021 618 | 1/1981 | ........................ 2/8 |
| EP | 0 213 799 A1 | 3/1987 | |
| EP | 0 264 208 A2 | 4/1988 | |
| EP | 0 268 498 | 5/1988 | ........................ 8/14 |
| EP | 0 351 100 A2 * | 1/1990 | |
| EP | 0 397 410 | 11/1990 | ........................ 8/14 |
| EP | 0 268 498 B1 | 10/1992 | |
| FR | 2 355 929 | 2/1978 | |
| GB | 783755 | 9/1957 | |
| GB | 940766 | 11/1963 | |
| GB | 1 535 166 | 12/1978 | .................. 103/66 |
| JP | 47017626 | 10/1966 | |
| JP | 72-03734 B | 2/1973 | |
| JP | 51131539 | 11/1976 | |
| JP | 56-141308 A | 11/1978 | |
| JP | 54014631 | 6/1979 | |
| JP | 56-161413 A | 11/1981 | |
| JP | 58-84819 A | 5/1983 | |
| JP | 62-69898 A | 3/1987 | |

(List continued on next page.)

OTHER PUBLICATIONS

DuPont "Material Safety Data Sheet", printed Apr. 9, 1998, pp. 1–2.
Buchholz, "Keeping Dry with Superabsorbent Polymers", *Chemtech* pp. 38–43 (Sep. 1994).
*Chemical Abstracts* vol. 96, No. 20, p. 35 (May 1982) Abstract No. 1636499, which is an English language abstract of JP 56–161413 A.

*Primary Examiner*—Susan W. Berman
(74) *Attorney, Agent, or Firm*—Smith Moore LLP

(57) ABSTRACT

A composite of a substrate having an application of superabsorbent polymer. The composite is made by applying, directly onto the substrate, an application of a polymer that will, upon being subjected to radiation, convert to a superabsorbent polymer. The substrate with applied polymer is subjected to radiation, such as being heated at a sufficient temperature for a sufficient time, to obtain the composite of substrate with superabsorbent polymer adhered to it.

48 Claims, 1 Drawing Sheet

FOREIGN PATENT DOCUMENTS

| | | |
|---|---|---|
| JP | 63-28912 A | 2/1988 |
| JP | 03042312 | 6/1991 |
| JP | 45018580 | 8/1993 |
| JP | 06041870 | 2/1994 |
| JP | 06206979 | 7/1994 |
| JP | 07082452 | 3/1995 |
| JP | 07171500 | 7/1995 |
| JP | 07242853 | 9/1995 |
| WO | WO96/23024 | 8/1996 |
| WO | WO99/10591 | 3/1999 |

\* cited by examiner

POLYMERS THAT ARE CROSS-LINKABLE TO FORM SUPERABSORBENT POLYMERS

TECHNICAL FIELD

The present invention relates, in general, to polymers that absorb aqueous liquids (such as water, blood, and urine) and especially, relates to superabsorbent polymers, which are those absorbent polymers that are capable of absorbing over 10 times their weight in water. More particularly, the present invention relates to pre-superabsorbent polymers that will, upon being subjected to radiation, such as heating, cross-link to form superabsorbent polymers.

DEFINITIONS OF ABBREVIATIONS

Definitions of Abbreviations

| Abbreviations | Definitions |
| --- | --- |
| X-linking | cross-linking |
| SAP | superabsorbent polymer, a polymer which absorbs over 10 times its weight in water |
| pre-SAP | a polymer which is not a SAP and which is capable upon as heating, becoming a SAP |
| CAA | composite absorbency ability |
| CRC | centrifuge retention capacity |
| $H_2O_2$ | hydrogen peroxide |
| GAA | glacial acrylic acid |
| PA | polyacrylate |
| HPA | hydroxypropyl acrylate |
| N-MMA | N-methylol methacrylamide |
| NaOH | sodium hydroxide |
| 2-ME | 2-mercaptoethanol |
| DI | deionized |
| mg | milligram |
| ml | milliliter |
| g | gram |
| mm | millimeter |
| cm | centimeter |
| psi | pounds per square inch |
| ppm | parts per million |
| VOC | volatile organic compound |
| UV | ultraviolet |

BACKGROUND OF THE INVENTION

General background on the manufacture of superabsorbent polymers can be seen in the journal article, "Keeping Dry with Superabsorbent Polymers", Chemtech, (September 1994) by Buchholz. This article contains an excellent discussion of the conventional methods for making superabsorbent polymers, certain of which have sulfonate functional groups and certain of which have carboxylic acid functional groups. Also mentioned are various uses for superabsorbent polymers, such as in a disposable diaper, in a sealing composite between concrete blocks that make up the wall of underwater tunnels, and in tapes for water blocking in fiber optic cables and power transmission cables.

More general background with respect to various superabsorbent polymers and their methods of manufacture can be seen in U.S. Pat. No. 5,229,466 (issued Jul. 20, 1993) to Brehm and Mertens; U.S. Pat. No. 5,408,019 (issued Apr. 18, 1995) to Mertens, Dahmen and Brehm; and U.S. Pat. No. 5,610,220 (issued Mar. 11, 1997) to Klimmek and Brehm, all of which patents are assigned to Chemische Fabrik Stockhausen GmbH.

Another good background discussion of the methods for making superabsorbent polymers can be seen in U.S. Pat. No. 5,409,771 (issued Apr. 25, 1995) to Dahmen and Mertens, assignors to Chemische Fabrik Stockhausen GmbH. More specifically, this patent mentions that commercially available superabsorbent polymers are generally X-linked polyacrylic acids or X-linked starch-acrylic-acid-graft-polymers, the carboxyl groups of which are partially neutralized with sodium hydroxide or caustic potash. Also mentioned is that the superabsorbent polymers are made by two methods. One method is the solvent polymerization method and the other method is the inverse suspension or emulsion polymerization method.

In the solvent polymerization method, an aqueous solution of partially neutralized acrylic acid, for instance, and a multi-functional network X-linking agent is converted to a gel by radical polymerization, typically followed by a heat treatment. The resultant is dried, ground and screened to the desired particulate size.

In the inverse suspension or emulsion polymerization method, an aqueous solution of partially neutralized acrylic acid, for instance, is dispersed in a hydrophobic organic solvent by employing colloids or emulsifiers. Then, the polymerization is started by radical initiators. Water is azeotropically removed from the reaction mixture after completion of the polymerization, typically followed by a heat treatment. The resultant product is then filtered and dried. Network X-linking is typically achieved by dissolving a polyfunctional X-linking agent in the monomer solution.

More specifically with regard to use of heat to effect X-linking, EP Patent Application Publication No. 0 397 410 A2 (published Nov. 14, 1990) to Allen, assignor to Allied Colloids Limited, describes a water soluble, substantially linear, polymer made by co-polymerization of a water soluble blend of monoethylenically unsaturated monomers comprising carboxylic acid monomers such as acrylic acid and a hydroxylic monomer of the formula $CHR^1=CR^2-Y-M_a-OH$, where $R^1$ is hydrogen or carboxy; $R^2$ is hydrogen, carboxy, or methyl; Y is oxygen, $CH_2O$, or COO; M is alkyleneoxy; and a is at least 5. After the polymer is shaped by extrusion or other shaping of an aqueous solution of the polymer, the polymer is X-linked, such as by heating above 150° C., typically at 220° C., to form X-linkages between the carboxyl and hydroxyl groups. The shaped resultant is described as being useful for diapers, catamenial appliances (i.e., sanitary napkins), incontinence pads, and bandages. EP Patent Application Publication No.0 397 410 A2 has priority to GB 8910788, which is one of several GB applications to which U.S. Pat. No. 5,147,956 (issued Sep. 15, 1992) and U.S. Pat. No. 5,280,079 (issued Jan. 18, 1994), both assigned to Allied Colloids Limited, have priority.

Moreover, EP Patent Application Publication No. 0 397 410 A2 states that achieved are higher and more reproducible absorption characteristics than in EP Patent Application Publication No.0 268 498 A2 (published May 5, 1988) to Allen, Farrar, and Flecher, assignors to Allied Colloids Limited. EP No. 0 268 498 A2 is a counterpart of U.S. Pat. No. 4,962,172 (issued Oct. 9, 1990), assigned to Allied Colloids Limited. Each of U.S. Pat. Nos. 5,147,956 and 5,280,079 is a Continuation-in-Part leading back to the U.S. application that matured into U.S. Pat. No. 4,962,172.

Additionally, U.S. Pat. No. 4,057,521 (issued Nov. 8, 1977) to Gross, assignor to The Dow Chemical Company, shows water swellable absorbent articles, made from copolymers having a copolymerized crosslinker, together with methods for their preparation, and a composition containing a copolymerized crosslinker useful to make said articles. The articles are crosslinked by heating and/or removing substantially all of the water from the precursor composition. The absorbent articles are useful as surgical sponges, diapers, tampons, meat trays, bath mats, and the like.

Furthermore, U.S. Pat. No. 5,534,304 to Geursen and Willemsen, assignors to Akzo Nobel NV, shows a process for treating a substrate, namely a fibre or a fibrous product, with a superabsorbent material, in which process there is applied to the surface of the substrate, which is not an aramide fibre, a layer of a water-in-oil emulsion which contains a superabsorbent material in its aqueous phase, so that there is applied to the substrate, calculated on its dry weight, 0.3 to 40 wt. % of the superabsorbent material, after which the liquid constituents of the emulsion are wholly or partially removed from the substrate.

Also of interest are U.S. Pat. No. 4,812,491 (issued Mar. 14, 1989) to Hahn, assignor to the Glidden Company, and EP Published Patent Application No. 0 021 618 A1 (published Jan. 7, 1981) to Backhouse and Palluel, assignors to Imperial Chemical Industries Limited, both of which describe suspension polymers useful as paint coatings. More particularly, the U.S. patent involves a process for producing a self-curing paint coating composition that requires co-polymerizing ethylenically unsaturated monomers, such as carboxyl or hydroxyl functional monomers and also alkylol acrylamide monomer (but excluding amine monomers), followed by treating the resultant with an ion exchange resin to remove cations from the emulsion polymer and produce a pH of less than 2.5 in order to produce a thermoset paint coating film. The European publication involves a process for the production of X-linked addition polymer microparticles made from the dispersion polymerization of ethylenically unsaturated monomers in an aliphatic hydrocarbon liquid in the presence of a specific stabilizer. The process requires that at least one of the monomers contains hydroxymethylamino or alkoxymethylamino and at least one other monomer contains hydroxyl or carboxyl. The resultant microparticles are incorporated into paint coating compositions.

As is well known, one use for superabsorbent polymers is in making tapes for water blocking when a tape is placed alongside fiber optic filaments in an end use communications cable. Thus, additionally of note is U.S. Pat. No. 5,642,452 (issued Jun. 24, 1997) to Gravely, Stokes. and Tanaka, assignors to Sumitomo Electric Lightwave Corporation. This patent describes an optical fiber communications cable that is manufactured absent the use of a viscous water blocking compound. Rather, a water swellable yarn is helically wrapped around the central strength member in order to absorb water that may become present between the strength member and the buffer tubes of the cable. Also, a water swellable tape is disposed between the core and the jacket of the cable to absorb water that may become present between the buffer tubes and elements overlaying the core of the cable. The patent describes the strength member as being formed from aramide or glass, and most suitably formed of KEVLAR®, a trademark for a type of aramide sold by DuPont Corporation of Wilmington, Del. Also, the patent describes that the water blocking yarn and water swellable tape are made from polyester.

The disclosures of all of the above-mentioned patents and published patent applications are incorporated by reference.

SUMMARY AND OBJECTS OF THE INVENTION

Nevertheless, a need still exists to obviate making tapes of superabsorbent polymer particles, as described in U.S. Pat. No. 5,642,452 mentioned above. Industry would be given a great advantage if strands of various materials (or alternatively, the fiber optic filaments) could be dip coated into an aqueous solution of the pre-superabsorbent polymer, followed by heating the polymer in order to convert it into a superabsorbent polymer coating on the strands (or alternatively, on the fiber optic filaments). In particular, coating the fiber optic filaments obviates the many problems with placing the tapes and fiber optic filaments together.

Therefore, the present invention provides a method for making a composite of a substrate having an application of superabsorbent polymer that is adhered to the substrate. The method comprises first preparing an aqueous solution of a polymer which is capable, upon being subjected to radiation from a radiation source for a sufficient time, of becoming a superabsorbent polymer. Preferably, the radiation source provides UV rays and/or heat. Then, the aqueous solution is applied to a substrate. Next, the resultant of the substrate with the applied aqueous solution is subjected to the radiation source, for instance heated for a sufficient time at a sufficient temperature, to convert the polymer to a superabsorbent polymer. Obtained is a composite of a substrate having a coating of superabsorbent polymer adhered to the substrate. Typically, the superabsorbent polymer is water insoluble.

Preferably, the polymer has functional groups that crosslink upon being subjected to the radiation source, such as UV rays and/or heat, in order to form the superabsorbent polymer. More preferably, in one embodiment, the polymer has a network cross-linking agent that is an alkylol methacrylamide, which is believed to allow for heating at relatively low temperatures of about 140° C. or less for the conversion to a superabsorbent polymer.

Accordingly, it is an object of the present invention to provide a method for making composites of a substrate coated with a superabsorbent polymer, wherein the preferred low temperature embodiment saves energy as compared to high temperature methods.

Hence, advantageously with the lower temperature embodiment, the curing oven, that is used for converting the polymer to a superabsorbent polymer via heat, can have a higher throughput.

Furthermore, it is an advantage of the lower temperature embodiment that many more kinds of substrates that would be ruined by the higher temperatures can be used.

Another advantage of the lower temperature embodiment is that the superabsorbent polymer component of the composite often exhibits a desirably high CRC, and typically, the CRC with D1 water will be approximately 45 g/g.

One more advantage, particularly with the higher temperature embodiment, is sea water stability of the superabsorbent polymer, as further illustrated in Example C below.

Some of the objects and advantages of the invention having been stated, other objects and advantages will become evident as the description proceeds, when taken in connection with the Laboratory Examples described below.

DETAILED DESCRIPTION OF THE INVENTION

Figure 1:
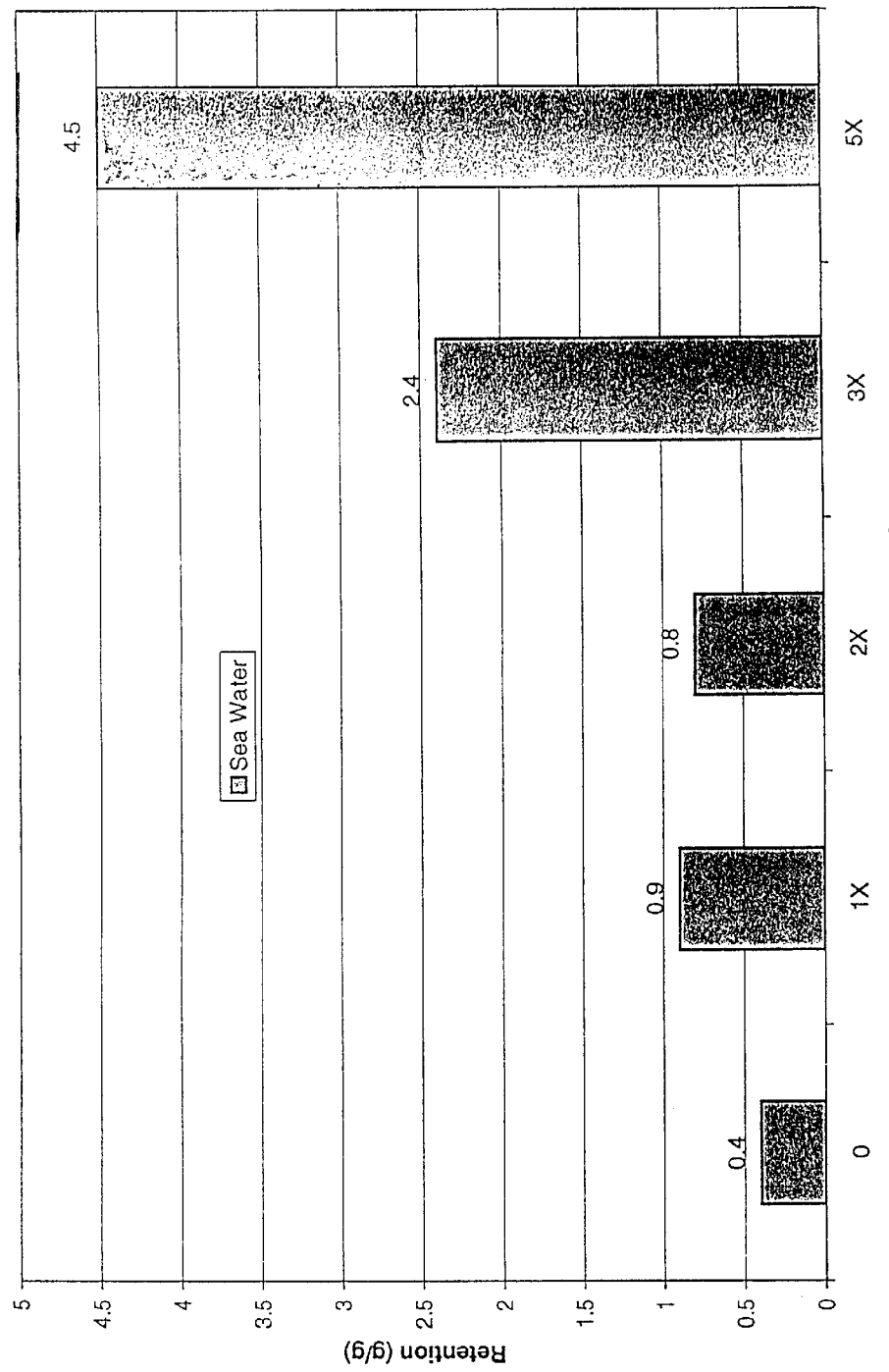
FIG. 1 is a bar graph illustrating the results of the CRC tests from the SAPs of Example C.

As long as the above-mentioned pre-SAP is capable upon heating at a sufficient time and at a sufficient temperature of becoming a SAP (preferably, the pre-SAP has functional groups that will, upon provision of a sufficient amount of heating for a sufficient time, X-link to convert the pre-SAP into a SAP), the SAP may be manufactured by any of the prior art polymerization processes for making the SAPs.

Preferably, the pre-SAP is water soluble, a solvent polymerization process is employed to make the SAP, and the SAPs made this way are called solvent polymerization SAPs.

Additionally, it is contemplated that any of the prior art emulsion or suspension polymerization processes may be employed to make the SAP with the following condition. Since by definition an emulsion polymer is a water-and-polymer suspension in a hydrophobic medium, then the pre-SAP would be water insoluble. Hence, a surfactant would have to be present in order to make the pre-SAP be in a water soluble form, i.e., in order to emulsify the aqueous monomer solution in the oil phase prior to polymerization. Suitable surfactants for use in the present invention are well known to those of skill in the art of emulsion polymerization. The SAPs made this way are called emulsion polymerization SAPs.

Thus, by the term "aqueous solution" of the polymer (i.e., of the pre-SAP) is meant to include a true aqueous solution, as well as to include an aqueous suspension that has present in it a surfactant in order to cause the polymer (i.e., the pre-SAP) to be in a water soluble form.

Thus, the SAP may be obtained by polymerizing at least about 10%, more preferably about 25%, even more preferably about 55 to about 99.9%, by weight of monomers having olefinically-unsaturated carboxylic and/or sulfonic acid groups. Such acid groups include, but are not limited to, acrylic acid, methacrylic acid, 2-acrylamido-2-methylpropane sulfonic acid, and mixtures thereof. The acid groups are present partially as salts, such as sodium, potassium, or ammonium salts.

The acid groups are typically neutralized to at least about 25 mol %, more preferably at least about 50 mol %. More particularly, the preferred SAP has been formed from X-linked acrylic acid or methacrylic acid, which has been neutralized to an extent of about 50 to about 80 mol %, more preferably about 60 to about 70 mol %. Suitable neutralizing agents are hydroxides and/or carbonates of alkaline earth metals and/or alkali metals, for instance, NaOH. Neutralization of acid groups may be performed prior to the polymerization to form the pre-SAP, may be performed on the pre-SAP, or a combination thereof.

Additional useful monomers for making the SAPs include from above 0 up to about 60% by weight of acrylamide, methacrylamide, maleic acid, maleic anhydride, esters (such as hydroxyethyl acrylate, hydroxypropyl acrylate, hydroxyethyl methacrylate, hydroxypropyl methacrylate, glycidyl methacrylate, and dimethyl-aminoalkyl-methacrylate), dimethyl-aminopropyl acrylamide, and acrylamidopropyl trimethyl-ammonium chloride. Percentages below about 60% of these monomers are desirable as percentages above 60% typically will have a detrimental effect and deteriorate the swell capacity of the resultant SAP. A preferred amount is from about 1% to about 55%, more preferably, from about 1% to about 25% by weight, and even more preferably from about 2% to about 10% by weight. A suitable hydroxypropyl acrylate for use in the present invention is sold under the trade name Mhoromer AM 438 by Creanova, Inc. Such monomers may be present whether or not a network X-linking agent as described in the next paragraph, is present.

Suitable network X-linking agents that may be used in making the SAPs are those which have 1 ethylenically unsaturated double bond and 1 functional group reactive toward acid groups, and those which have several functional groups reactive toward acid groups. Very minor amounts of network X-linking agents which have at least 2 ethylenically unsaturated double bonds may also be used to enhance performance. Suitable kinds of network X-linking agents include, but are not limited to, acrylate and methacrylate of polyols (such as butanediol diacrylate, polyglycol diacrylate, hexanediol dimethacrylate, tetrahydrofurfuryl-2-methacrylate, glycerol dimethacrylate, trimethylolpropane triacrylate, allyloxy polyethylene glycol methacrylate, and ethoxylated trimethylolpropane triacrylate), allyl acrylate, diallyl acrylamide, triallyl amine, diallyl ether, N-methylol acrylamide, methylenebisacrylamide, glycerol dimethacrylate, N,N-dimethylaminoethyl methacrylate, N-dimethylaminopropyl methacrylamide, and N-methylol methacrylamide. The last is very suitable for use in the present invention and is sold under the trade name: BM 818 by Creanova, Inc. In the embodiment where one or more of these network X-linking agents is not employed (see, Example B below), then one or more of the monomers noted in the previous paragraph may effect network X-linking.

A radiation source may be operatively associated with the method to provide radiation to the pre-SAP which converts it into a SAP. The radiation may be selected from the group consisting of infrared rays, visible rays, ultraviolet rays, x-rays, gamma rays, beta particles, high energy electrons, heat (i.e., from an oven), or combinations thereof. Appropriate sources of radiation are commercially available.

In the preferred embodiment of the invention, the SAP is formed by heating the pre-SAP.

More preferably, heating may be conducted in the presence of an alkylol methacrylamide as a network X-linking agent, which causes functional groups, such as hydroxyl and/or carboxyl present in the pre-SAP to X-link and form the SAP. A typical temperature range for the network X-linking to convert the pre-SAP into a SAP ranges from about 100 to about 140° C., more preferably from about 110 to about 135° C. and most preferably from about 120 to about 130° C. While it is not intended to be bound to any theory, it is believed that the presence of an alkylol methacrylamide, such as N-methylol methacrylamide, as a network X-linking agent is what allows for achieving the reaction with the temperature under about 140° C.

Network X-linking agents, as defined herein, need not be used. In that event, the heating to convert the pre-SAP into the SAP should be from about 140° C. to about 200° C. or even higher, preferably about 160° C., and more preferably about 180° C.

Regardless of whether a network X-linking agent, as defined herein, is present or not, the time for heating typically is from about 30 seconds to about 60 minutes. A time of about 1 to about 50 minutes is very typical. The specific time and temperature are not critical, as long as they are sufficient to X-link the pre-SAP and convert it into a SAP.

As described further below, prior to subjecting the pre-SAP to radiation, the pre-SAP is applied, such as by painting, rolling, printing (i.e., dot printing), spraying, brushing, swabbing, or dip coating, onto a substrate to form an application of the pre-SAP on the substrate, followed by the radiation conversion step into a SAP. After the radiation conversion step, the resultant is a composite of the substrate coated with the SAP.

Suitable substrates for the inventive composite include various yarns, tapes, wovens, non-wovens, films, fluff pulps, protective sheaths, and fibers or filaments. Aramide yarns, glass fiber, polyester, polypropylene, polyamide, polyethylene, or cellulose, among others, are particularly suitable materials for the substrate.

Furthermore, depending on the desired end use (i.e., the particular kind of substrate onto which the pre-SAP is applied and then dried), the SAP may have a water soluble polymeric component. The content may range from above 0 up to about 30% by weight of a component that includes, but is not limited to, partially or completely saponified polyvinyl alcohol, polyvinyl pyrrolidone, starch, starch derivatives, polyglycols, polyacrylic acids, and combinations thereof. The molecular weight of the component is not critical, provided that it is water soluble. Preferred water soluble polymeric components are starch, polyvinyl alcohol, and mixtures thereof. Preferably, the content of the water soluble polymeric component in the SAP ranges from about 1 to about 5% by weight, especially if starch and/or polyvinyl alcohol are present as the water soluble polymeric component. Also, the water soluble polymeric component may be present as a graft polymer having the acid-groups-containing polymer.

In connection with the particle shape of the SAP, there are no specific limitations. The reason is that the SAP will be in the form of a coating on a substrate, such as a yarn, as illustrated further below in the Laboratory Examples, instead of the SAP being the dried resultant obtained by solvent or solution polymerization, or by emulsion or suspension polymerization.

Various end use absorbent products that may contain a composite of the inventive SAP applied on a substrate include, but are not limited to, agricultural products (i.e., a polymer with herbicide and/or insecticide), fiber optic cables, power cables, water blocking tapes, insulation, feminine care products (i.e., sanitary napkins and/or tampons), incontinence items for adults, diapers for babies, paper towels, sealing composites between concrete blocks, bandages, surgical sponges, meat trays, bath mats, and the like.

To characterize the SAPs as set out in the Laboratory Examples below (both those superabsorbent polymers of the present invention, as well as those comparison, superabsorbent polymers), the composite absorbency ability (CAA) and the centrifuge retention capacity (CRC) were measured in the following manner.

CAA Test Using Aramide Yarn. The test was conducted at ambient conditions of room temperature and pressure. The water absorbency ability of aramide polymeric fibrous water-blocking yarns coated with SAP was measured by this method and reported as the mass of water absorbed (in grams) per gram of applied SAP.

A 600 ml sample of the aqueous solution of water soluble pre-SAP was placed as a bath in a beaker. Then, the CAA was determined in the following manner for a 1420 denier polymeric strand of aramide filament yarn that had been coated with pre-SAP and heated to convert the coating into a SAP coating. Other kinds of radiation, as described above, may be employed for converting the pre-SAP into a SAP.

Specifically, a strand of yarn was collected on a polyvinyl chloride spool that already had been weighed. The spool with the yarn was re-weighed in order to determine the dry weight of the yarn, which was about 2.5 g.

Then, 2 glass stirring rods that had been banded together at 1 respective end of each were employed to draw the yarn through the pre-SAP bath and between the rods to remove excess pre-SAP from the yarn, followed by collecting the yarn now coated with wet pre-SAP onto a second polyvinyl chloride spool.

The coated wet yarn was then placed on a hanger, which was then placed for 10 minutes inside of a pre-heated oven at 120° C. (Alternative times and temperatures may be used, as discussed above, to facilitate optimum conversion of pre-SAP into SAP.) Next, the hanger with the yarn having a now dried coating, which had been converted by the heat of the oven into a SAP due to the thermal X-linking, was removed from the hanger.

The SAP coated yarn was weighed and the % dry add on was calculated by subtracting the weight of the yarn from the weight of the yarn coated with the SAP, and dividing by the weight of the yarn coated with the SAP.

The CAA is defined to be the mass of water absorbed (in grams) per gram of SAP, which has been applied to a substrate, in this case the aramide filament yarn. A 2.0 gram composite (substrate and applied SAP) specimen was placed in 100 grams of Dl water. After 10 minutes, this mixture was poured onto a paper filter, allowing the free non-absorbed water to drain into a vacuum-aspirated filter flask. This filtrate was then transferred to a 100 ml graduated cylinder to measure the quantity of filtrate. The CAA was then calculated using the following formula:

$$CAA = [(100 - B)]/[A \cdot W]$$

where:

100 = grams of water $B$ = grams of filtrate poured into graduated cylinder $W$ = weight of composite specimen of yarn with coating of SAP $A$ = % dry add on of SAP onto substrate CRC Test. The test was conducted at ambient conditions of room temperature. Retention of Dl water was determined according to the tea bag test method and reported as an average value of 2 measurements. Approximately 200 mg of SAP particles, that had been sieved to a particle size distribution ranging from about 300 to 600 micrometers, were enclosed in a tea bag and immersed in the Dl water for 30 minutes. Next, the tea bag was centrifuged at 1600 rpm for 3 minutes and weighed. The diameter of the centrifuge apparatus was about 20 cm. Also, 2 tea bags without particles were used as blanks.

Then, the CRC property (measured in grams of liquid absorbed per gram of particles) was calculated according to the following equation.

$$CRC = (W_3 - W_2 - W_1)/W_1$$

where:

CRC=retention after 30 minutes immersion time $W_1$=initial weight in grams of SAP particles $W_2$=average weight in grams of two blanks after centrifugation $W_3$=weight in grams of test tea bag after centrifugation

LABORATORY EXAMPLES

In the following examples, each SAP was a X-linked sodium polyacrylate made by solvent polymerization. Also, each percentage recited was a weight % unless specifically indicated otherwise as a mol %.

Example A
(One Embodiment of the Present Invention)

A 1500 gram sample of aqueous solution containing a polymer that was thermally X-linkable, i.e., containing a pre-SAP, was prepared. Because the pre-SAP was totally water soluble and formed a true aqueous solution, it is believed that the pre-SAP was substantially linear, rather than branched. However, no quantitative test to determine linearity was employed.

After drying as indicated below, the resultant SAP was:

| | |
|---|---|
| sodium acrylate | 62.6% |
| acrylic acid | 17.2% |
| HPA | 15.6% |

N-MMA 4.6%

A 600 ml sample of the aqueous solution of water soluble pre-SAP was placed as a bath in a beaker. Then, the CAA described above was employed in the following manner for a 1420 denier polymeric strand of aramide yarn that had been coated with pre-SAP and heated to convert the coating into a SAP coating.

Specifically, a strand of yarn was collected on a polyvinyl chloride spool that already had been weighed. The spool with the yarn was re-weighed in order to determine the dry weight of the yarn, which was about 2.5 g.

Then, 2 glass stirring rods that had been banded together at 1 respective end of each were employed to draw the yarn through the pre-SAP bath and between the rods to remove excess pre-SAP from the yarn, followed by collecting the yarn now coated with wet pre-SAP onto a second polyvinyl chloride spool.

The coated wet yarn was then placed on a hanger, which was then placed for 10 minutes inside of a pre-heated oven at 120° C. Next, the hanger with the yarn having a now dried coating, which had been converted by the heat of the oven into a SAP due to the thermal X-linking of the hydroxypropyl acrylate and the N-methylol methacrylamide, was removed from the hanger.

The SAP coated yarn was weighed and the % dried add on was calculated by subtracting the weight of the yarn from the weight of the yarn coated with the SAP, and dividing by the weight of the yarn coated with the SAP.

Using the formula CAA=[(100−B]/[A·W], the CAA determined by this method was found to be 29.6 g/g.

Next, in order to determine the CRC of the SAP, a 5 gram sample of the aqueous solution of pre-SAP was weighed into an aluminum pan, followed by placing the pan with the sample in an oven at 120° C. for 2 hours. The now dried material, which had been converted by the heat of the oven into a SAP, was removed from the pan and milled at 10,000 rpms using a 5 mm ring sieve. A portion of the milled material was sieved and a sample with a particle size range from 300 to 600 micrometers was collected. The CRC was then tested as described above with DI water, and found to be 45 g/g.

Example B
(Another Embodiment of the Present Invention)

The procedure of Example A was repeated with the following changes to make SAP.

No N-MMA or other network X-linking agent was used.

Also, instead of making X-linked sodium polyacrylate, the resultant SAP made was X-linked sodium polyacrylate-acrylamide.

Also, the heating to convert the pre-SAP into a SAP was conducted for 20 minutes at 180° C., instead of 10 minutes at 120° C.

The resultant SAP (dried from the heating at 130° C.) comprised 65.8% by weight of sodium acrylate, 14.2% by weight of acrylic acid, 5% by weight of hydroxyethyl methacrylate, 5% by weight of hydroxy propyl methacrylate, 5% by weight of hydroxyethyl acrylate, and 5% by weight of hydroxy propyl acrylate, prepared as a 36% solution in water.

The CAA was 23.1 g/g and the CRC was 23.3 g/g.

Example C
(Another Embodiment of the Present Invention)

The procedure of Example A was repeated with the following changes to make SAP.

No N-MMA or other network X-linking agent was used.

Also, instead of making X-linked sodium polyacrylate, the resultant SAP made was X-linked sodium polyacrylate-acrylamide (except for Test 1 below which had 0% acrylamide co-monomer for comparison).

Also, the heating to convert the pre-SAP into a SAP was conducted for 20 minutes at 180° C., instead of 10 minutes at 120° C.

The following SAPs were made, where the % amounts reflect the various ingredients in the resultant dried SAP.

| Test 1. | |
|---|---|
| 0% Acrylamide | |
| Sodium Acrylate | 66.5% |
| Acrylic Acid | 22.3% |
| Acrylamide | 0% |
| Hydroxyethyl acrylate | 11.2% |
| Hydroxypropyl acrylate | (total hydroxylic monomers) |
| Hydroxyethyl methacrylate | |
| Hydroxypropyl methacrylate | |

| Test 2. | |
|---|---|
| 1X Acrylamide | |
| Sodium Acrylate | 60.0% |
| Acrylic Acid | 20.0% |
| Acrylamide | 6.0% |
| Hydroxyethyl acrylate | 14.0% |
| Hydroxypropyl acrylate | (total hydroxylic monomers) |
| Hydroxyethyl methacrylate | |
| Hydroxypropyl methacrylate | |

| Test 3. | |
|---|---|
| 2X Acrylamide | |
| Sodium Acrylate | 56.0% |
| Acrylic Acid | 19.0% |
| Acrylamide | 12.0% |
| Hydroxyethyl acrylate | 13.0% |
| Hydroxypropyl acrylate | (total hydroxylic monomers) |
| Hydroxyethyl methacrylate | |
| Hydroxypropyl methacrylate | |

| Test 4. | |
|---|---|
| 3X Acrylamide | |
| Sodium Acrylate | 50.2% |
| Acrylic Acid | 17.0% |
| Acrylamide | 18.0% |
| Hydroxyethyl acrylate | 13.8% |
| Hydroxypropyl acrylate | (total hydroxylic monomers) |
| Hydroxyethyl methacrylate | |

-continued

Hydroxypropyl methacrylate

Test 5.

5X Acrylamide

| Sodium Acrylate | 35.7% |
|---|---|
| Acrylic Acid | 12.0% |
| Acrylamide | 36.0% |
| Hydroxyethyl acrylate | 16.3% |
| Hydroxypropyl acrylate | (total hydroxylic monomers) |
| Hydroxyethyl methacrylate | |
| Hydroxypropyl methacrylate | |

In order to evaluate the relative abilities of each of these formulations to absorb solutions, the above-described CRC test was conducted but with the following two changes. First, the aqueous solution contained various other dissolved electrolytes, in addition to NaCl, in order to simulate sea water. Second, each of the resultant SAPs was milled and sieved to particle size of less than 850 micrometers to greater than 150 micrometers instead of 300 to 600 micrometers. Each of these products was then evaluated with the simulated sea water solution, having the following components:

Recipe for simulated sea water

| Component | Weight % |
|---|---|
| Distilled water | 95.93% |
| Magnesium Sulfate (MgSO$_4$-7H$_2$O) | 0.68% |
| Sodium Chloride (NaCl) | 2.73% |
| Magnesium Chloride (MgCl$_2$-6H$_2$O) | 0.49% |
| Calcium Chloride (CaC$_2$-2H$_2$O) | 0.16% |
| Sodium Bicarbonate (NaHCO$_3$) | 0.019% |

The results of the CRC test with simulated sea water are summarized in the bar graph of FIG. 1. Clearly, the SAP with the 36% acrylamide co-monomer component (from Test 5) exhibited superior retention of the simulated sea water. This is surprising as SAPs often exhibit good retention in Dl water but poor retention in water containing many electrolytes, including multi-valent ions as well as mono-valent ions, like real sea water does. Thus, this SAP will be very useful for coating substrates to be used in the presence of liquids containing many electrolytes, including multi-valent and/or mono-valent ions, for instance, to be used for water blocking with fiber optic filaments laid in the ocean for transoceanic communication cables.

Example D
(Another Embodiment of the Present Invention)

Each of Examples A through C may be repeated except with using UV radiation instead of heat for converting the pre-SAP into a SAP. Similar results should be obtained.

Example E
(Comparison)

The procedure of Example 2, polymer 5, as per the above-noted EP No. 0 397 410 A2 may be repeated, including heating the polymer for 8 minutes at 220° C. to X-link it and to convert it thermally to a SAP. The CRC of SAP particles may then be tested as described above with aqueous 0.9 weight % saline, and should be 20 g/g.

It will be understood that various details of the invention may be changed without departing from the scope of the invention. Furthermore, the foregoing description is for the purpose of illustration only, and not for the purpose of limitation--the invention being defined by the claims.

What is claimed is:

1. A method for making a composite of a substrate having an application of superabsorbent polymer, said method comprising:
   (a) preparing an aqueous solution of a polymer which is formed from at least one monomer, where the polymer is capable upon being subjected to radiation from a radiation source of becoming a superabsorbent polymer;
   (b) applying the aqueous solution to a substrate;
   (c) subjecting the substrate having the applied aqueous solution to radiation from the radiation source for a sufficient time to convert the polymer into a superabsorbent polymer; and
   (d) obtaining a composite of a substrate having an application of superabsorbent polymer adhered to the substrate.

2. The method of claim 1, wherein the polymer has functional groups that cross-link upon being subjected to radiation to form the superabsorbent polymer.

3. The method of claim 1, wherein the superabsorbent polymer is formed from carboxylic acid monomer and hydroxylic monomer.

4. The method of claim 3, wherein the superabsorbent polymer is formed with network cross-linking.

5. The method of claim 4, wherein the network cross-linking is achieved with a network cross-linking agent.

6. The method of claim 5, wherein the network cross-linking agent is an alkylol methacrylamide.

7. The method of claim 1, wherein the superabsorbent polymer is formed from carboxylic acid monomer, hydroxylic monomer, and acrylamide monomer.

8. The method of claim 7, wherein the hydroxylic monomer is selected from the group consisting of hydroxyethyl acrylate, hydroxypropyl acrylate, hydroxyethyl methacrylate, hydroxypropyl methacrylate, and combinations thereof.

9. The method of claim 8, wherein the superabsorbent polymer is formed with network cross-linking and free of a network cross-linking agent.

10. The method of claim 1, wherein the substrate is in a form selected from the group consisting of a yarn, tape, woven, film, fluff pulp, protective sheath, fiber, filament, and combinations thereof.

11. The method of claim 1, wherein the substrate is a material selected from the group consisting of aramide, polyester, glass, polypropylene, polyamide, polyethylene, cellulose, and combinations thereof.

12. The method of claim 1, wherein the superabsorbent polymer is formed from a polymer made by solvent polymerization.

13. The method of claim 1, wherein the radiation is selected from the group consisting of infrared rays, visible rays, ultraviolet rays, x-rays, gamma rays, beta particles, high energy electrons, heat, and combinations thereof.

14. The method of claim 13, wherein the radiation is heat and the method consists essentially of:
   (a) preparing an aqueous solution of a polymer, where the polymer is capable upon heating of becoming a superabsorbent polymer;
   (b) applying the aqueous solution to a substrate;
   (c) heating the substrate having the applied aqueous solution for a sufficient time and at a sufficient temperature to convert the polymer into a superabsorbent polymer; and (d) obtaining a composite of a substrate having an application of superabsorbent polymer adhered to the substrate.

15. The method of claim 14, wherein the polymer has functional groups that cross-link upon heating to form the superabsorbent polymer.

16. The method of claim 14, wherein the heating in step (c) is conducted at a temperature of about 140° C. or less.

17. The method of claim 16, wherein the superabsorbent polymer is formed from carboxylic acid monomer and hydroxylic monomer.

18. The method of claim 17, wherein the superabsorbent polymer is formed with network cross-linking.

19. The method of claim 18, wherein the network cross-linking is achieved with a network cross-linking agent.

20. The method of claim 19, wherein the network cross-linking agent is an alkylol methacrylamide.

21. The method of claim 14, wherein the heating in step (c) is conducted at a temperature of about 140° C. or higher.

22. The method of claim 21, wherein the superabsorbent polymer is formed from carboxylic acid monomer, hydroxylic monomer, and acrylamide monomer.

23. The method of claim 22, wherein the hydroxylic monomer is selected from the group consisting of hydroxyethyl acrylate, hydroxypropyl acrylate, hydroxyethyl methacrylate, hydroxypropyl methacrylate, and combinations thereof.

24. The method of claim 23, wherein the superabsorbent polymer is formed with network cross-linking and free of a network cross-linking agent.

25. The method of claim 14, wherein the substrate is in a form selected from the group consisting of yarn, tape, woven, film, fluff pulp, protective sheath, fiber, filament, and combinations thereof.

26. The method of claim 14, wherein the substrate is a material selected from the group consisting of aramide, polyester, glass, polypropylene, polyamide, polyethylene, cellulose, and combinations thereof.

27. The method of claim 14, wherein the superabsorbent polymer is formed from a polymer made by solvent polymerization.

28. A composite comprising a substrate and a superabsorbent polymer adhered to the substrate, the composite prepared by the steps comprising of:

a) selecting a substrate; and b) coating the substrate with an aqueous solution of pre-superabsorbent polymer; and c) radiating the aqueous solution of pre-superabsorbent polymer for a sufficent time to convert the aqueous solution pre-superabsorbent polymer into a superabsorbent polymer adhered to the substrate.

29. The composite of claim 28, wherein the polymer has functional groups that cross-link upon being subjected to radiation to form the superabsorbent polymer.

30. The composite of claim 28, wherein the superabsorbent polymer is formed from carboxylic acid monomer and hydroxylic monomer or formed from carboxylic acid monomer, hydroxylic monomer, and acrylamide monomer.

31. The composite of claim 28, wherein the superabsorbent polymer is a network cross-linked sodium polyacrylate or network cross-linked polyacrylate-acrylamide.

32. The composite of claim 28, wherein the substrate is in a form selected from the group consisting of a yarn, tape, woven, film, fluff pulp, protective sheath, fiber, filament, and combinations thereof.

33. The composite of claim 28, wherein the substrate is a material selected from the group consisting of aramide, polyester, glass, polypropylene, polyamide, polyethylene, cellulose, and combinations thereof.

34. The composite of claim 28, wherein the superabsorbent polymer is formed from a polymer made by solvent polymerization.

35. An absorbent product containing the composite of claim 28.

36. The absorbent product of claim 35, wherein the product is selected from the group consisting of: agricultural products, fiber optic cables, power cables, water blocking tapes, insulation, feminine care products, incontinence items for adults, diapers for babies, paper towels, sealing composites between concrete blocks, bandages, surgical sponges, meat trays, and bath mats.

37. The composite of claim 28, wherein the radiation is selected from the group consisting of infrared rays, visible rays, ultraviolet rays, x-rays, gamma rays, beta particles, high energy electrons, heat, and combinations thereof.

38. The composite of claim 37, wherein the radiation is heat and the composite consists essentially of a substrate having an application of superabsorbent polymer adhered to the substrate, wherein the superabsorbent polymer consists essentially of a heat-treated polymer that converted, upon heating for a sufficient time at a sufficient temperature, into the superabsorbent polymer.

39. The composite of claim 38, wherein the polymer has functional groups that cross-link upon being subjected to radiation to form the superabsorbent polymer.

40. The composite of claim 38, wherein the superabsorbent polymer is formed from carboxylic acid monomer and hydroxylic monomer or formed from carboxylic acid monomer, hydroxylic monomer, and acrylamide monomer.

41. The composite of claim 38, wherein the superabsorbent polymer is a network cross-linked sodium polyacrylate or network cross-linked polyacrylate-acrylamide.

42. The composite of claim 38, wherein the substrate is in a form selected from the group consisting of a yarn, tape, woven, film, fluff pulp, protective sheath, fiber, filament, and combinations thereof.

43. The composite of claim 38, wherein the substrate is a material selected from the group consisting of aramide, polyester, glass, polypropylene, polyamide, polyethylene, cellulose, and combinations thereof.

44. The composite of claim 38, wherein the temperature is about 140° C. or less.

45. The composite of claim 38, wherein the temperature is about 140° C. or higher.

46. The composite of claim 38, wherein the superabsorbent polymer is formed from a polymer made by solvent polymerization.

47. An absorbent product containing the composite of claim 38.

48. A method for making a composite of a substrate and a superabsorbent polymer adhered to the substrate, said method comprising:

(a) preparing an aqueous solution of pre-superabsorbent polymer, where the aqueous solution of the pre-superabsorbent polymer is capable upon being subjected to radiation from a radiation source of becoming a superabsorbent polymer;

(b) applying the aqueous solution of the pre-superabsorbent polymer to a substrate;

(c) subjecting the substrate having the applied aqueous solution of the pre-superabsorbent polymer to radiation from the radiation source for a sufficient time to convert the pre-superabsorbent polymer into a superabsorbent polymer; and (d) obtaining a composite of a substrate having an application of superabsorbent polymer adhered to the substrate.

* * * * *